US00PP26475P2

(12) United States Plant Patent
Craigie et al.

(10) Patent No.: US PP26,475 P2
(45) Date of Patent: Mar. 8, 2016

(54) *AGAPANTHUS* PLANT NAMED 'PMB011'

(50) Latin Name: *Agapanthus orientalis*
Varietal Denomination: PMB011

(71) Applicants: John Maxwell Craigie, Pine Mountain (AU); Gail Alexis Craigie, Pine Mountain (AU)

(72) Inventors: John Maxwell Craigie, Pine Mountain (AU); Gail Alexis Craigie, Pine Mountain (AU)

(73) Assignee: Pine Mountain Botanics PTY. LTD., Pine Mountain, Queensland (AU)

( * ) Notice: Subject to any disclaimer, the term of this patent is extended or adjusted under 35 U.S.C. 154(b) by 216 days.

(21) Appl. No.: 13/998,903

(22) Filed: Dec. 19, 2013

(51) Int. Cl.
*A01H 5/02* (2006.01)

(52) U.S. Cl.
USPC ..... Plt./398

(58) Field of Classification Search
USPC ..... Plt./398
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Agapanthus* plant named 'PMB011', characterized by its compact and upright plant habit; vigorous growth habit; early flowering habit; numerous star-shaped flowers with violet blue and white-colored perianth segments arranged on upright and strong scapes; and ease of propagation.

3 Drawing Sheets

Botanical designation: *Agapanthus orientalis.*
Cultivar denomination: 'PMB011'.

BACKGROUND OF THE INVENTION

The present invention relates to a new and distinct cultivar of *Agapanthus* plant, botanically known as *Agapanthus orientalis* and hereinafter referred to by the name 'PMB011'.

The new *Agapanthus* plant is the product of a planned breeding program conducted by the Inventors in Pine Mountain, Queensland, Australia. The objective of the breeding program is to create new compact and vigorous *Agapanthus* plants with early flowering habit and attractive bi-colored flowers.

The new *Agapanthus* plant is the result of a cross-pollination made by the Inventors in 2009 of *Agapanthus orientalis* 'Snowflake', not patented, as the female, or seed, parent with a proprietary selection of *Agapanthus orientalis* known as code name PMB01, not patented, as the male, or pollen, parent. The new *Agapanthus* plant was discovered and selected by the Inventors as a single flowering plant from within the progeny of the stated cross-pollination in a controlled environment in Pine Mountain, Queensland, Australia during the spring of 2011.

Asexual reproduction of the new *Agapanthus* plant by divisions in a controlled environment in Pine Mountain, Queensland, Australia since the spring of 2011 has shown that the unique features of this new *Agapanthus* plant are stable and reproduced true to type in successive generations.

SUMMARY OF THE INVENTION

Plants of the new *Agapanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'PMB011'. These characteristics in combination distinguish 'PMB011' as a new and distinct *Agapanthus* plant:

1. Compact and upright plant habit.
2. Vigorous growth habit.
3. Early flowering habit.
4. Numerous star-shaped flowers with violet blue and white-colored perianth segments arranged on upright and strong scapes.
5. Ease of propagation.

Plants of the new *Agapanthus* differ primarily from plants of the female parent, 'Snowflake', primarily in perianth segment color as plants of 'Snowflake' have white-colored perianth segments.

Plants of the new *Agapanthus* differ primarily from plants of the male parent selection primarily in perianth segment color as plants of the male parent selection have violet blue-colored perianth segments.

Plants of the new *Agapanthus* can be compared to plants of *Agapanthus orientalis* 'PMN06', disclosed in U.S. Plant patent application Ser. No. 11/903,036. In side-by-side comparisons conducted in Pine Mountain, Queensland, Australia, plants of the new *Agapanthus* and 'PMN06' differed in the following characteristics:

1. Plants of the new *Agapanthus* were more compact than plants of 'PMN06'.
2. Plants of the new *Agapanthus* were more vigorous than plants of 'PMN06'.
3. Plants of the new *Agapanthus* had shorter and narrower leaves than plants of 'PMN06'.
4. Plants of the new *Agapanthus* had shorter scapes than plants of 'PMN06'.

5. Plants of the new *Agapanthus* had smaller flowers than plants of 'PMN06'.
6. Plants of the new *Agapanthus* flowered earlier than plants of 'PMN06'.

BRIEF DESCRIPTION OF THE PHOTOGRAPHS

The accompanying colored photographs illustrate the overall appearance of the new *Agapanthus* plant showing the colors as true as it is reasonably possible to obtain in colored reproductions of this type. Colors in the photographs may differ slightly from the color values cited in the detailed botanical description which accurately describe the colors of the new *Agapanthus* plant.

The photograph on the first sheet comprises a side perspective view of a typical flowering plant of 'PMB011' grown in a container.

The photograph on the second sheet is a close-up view of a typical inflorescence of 'PMB011'.

The photograph on the third sheet is a close-up view of a typical flower of 'PMB011'.

DETAILED BOTANICAL DESCRIPTION

The aforementioned photographs and following observations, measurements and values describe plants grown during the early spring (November) in 17.5-cm containers in a outdoor nursery in Pine Mountain, Queensland, Australia and under cultural practices typical of commercial *Agapanthus* production. During the production of the plants, day temperatures ranged from 3° C. to 38° C., night temperatures ranged from 3° C. to 27° C. and light levels ranged from 40 to 50 klux. Plants were one year old when the photographs and description were taken. In the following description, color references are made to The Royal Horticultural Society Colour Chart, 2007 Edition, except where general terms of ordinary dictionary significance are used.

Botanical classification: *Agapanthus orientalis* 'PMB011'.

Parentage:

*Female, or seed, parent.*—*Agapanthus orientalis* 'Snowflake', not patented.

*Male, or pollen, parent.*—Proprietary selection of *Agapanthus orientalis* identified as code number PMB01, not patented.

Propagation:

*Type.*—By tissue culture; plants of the new *Agapanthus* propagate relatively easily.

*Time to initiate roots, summer.*—About 10 to 14 days at temperatures about 28° C.

*Time to initiate roots, winter.*—About 10 to 14 days at temperatures about 22° C.

*Time to produce a rooted plant, summer.*—About 98 days at temperatures about 28° C.

*Time to produce a rooted plant, winter.*—About 126 days at temperatures about 22° C.

*Root description.*—Thick and fleshy; white in color.

*Rooting habit.*—Low branching; medium density.

Plant description:

*Plant form and growth habit.*—Evergreen flowering perennial plant; compact and upright plant habit and strong upright flower scapes; leaves and flowering stems basal; vigorous growth habit.

*Plant height* (*soil level to top of foliar plane*).—About 22 cm.

*Plant height* (*soil level to top of floral plane*).—About 40 cm.

*Plant width* (*spread*).—About 36 cm.

Leaf description:

*Arrangement and appearance.*—Leaves arranged in a basal rosette with about 21 leaves developing per plant; leaves distichous, simple and sessile; leaves erect to semi-erect in attitude.

*Leaf length.*—About 22 cm.

*Leaf width.*—About 1.8 cm.

*Shape.*—Ligulate.

*Apex.*—Broadly acute.

*Base.*—Cuneate.

*Margin.*—Entire.

*Texture, upper and lower surfaces.*—Smooth, glabrous.

*Venation pattern.*—Parallel.

*Color.*—Developing leaves, upper and lower surfaces: Close to N137A. Fully expanded leaves, upper and lower surfaces: Close to N137A; venation, close to N137A.

Flower description:

*Flower type and flowering habit.*—Single star-shaped flowers arranged in terminal umbels supported by strong upright scapes; flowers face mostly outwardly; umbels roughly hemispherical in shape; freely flowering habit with about 55 flowers developing per umbel.

*Fragrance.*—None detected.

*Natural flowering season.*—Relatively early flowering habit; under natural conditions, plants of the new *Agapanthus* being flowering during the middle spring in southeastern Queensland, Australia; plants propagated via micropropagation begin flowering about eight months after planting.

*Postproduction longevity.*—Flowers last about three to four weeks on the plant; flowers not persistent.

*Flower buds.*—Height: About 2.5 cm. Diameter: About 6 mm to 7 mm. Shape: Oblanceolate. Color: Close to 155B with close to 154B along perianth segment keels; with development, violet blue coloration, close to 92D, begins to appear proximally and darkens to close to 92C as the flowers begin to open.

*Inflorescence height.*—About 9 cm to 10 cm.

*Inflorescence diameter.*—About 12 cm.

*Flower diameter.*—About 2.6 cm.

*Flower depth.*—About 3 cm.

*Perianth.*—Quantity and arrangement: Typically six segments arranged in a single whorl; lower part of a segment is fused into a narrow tube; upper part of a segment is free and flaring outwardly. Segment length: About 1.8 cm. Segment width: About 8 mm. Segment lobe shape: Obovate. Segment apex: Broadly acute. Segment margin: Entire. Segment texture, upper and lower surfaces: Smooth, glabrous. Segment color, mature flower: Inner surface: Close to NN155D. Outer surface: Towards the base, between 91B to 92B; towards the apex, close to NN155D; occasionally, margins faintly traced with close to 91C; with subsequent development, basal color darkens to close to 92A.

*Peduncles* (*scapes*).—Length: About 40 cm. Diameter: At the base, close to 1.1 cm; at mid-section, about 7 mm. Strength: Strong. Aspect: Mostly upright. Texture: Smooth, glabrous. Color: Close to 146A.

*Pedicels.*—Length: About 3.7 cm. Diameter: About 1.7 mm. Aspect: Upright to horizontal from the peduncle axis. Strength: Strong. Texture: Smooth, glabrous. Color: Close to 144A to 144B.

*Reproductive organs.*—Stamens: Quantity per flower: Typically six. Filament length: About 3 cm. Filament color: Close to NN155D. Anther shape: Oblong; dorsifixed. Anther length: About 1 mm to 1.5 mm. Anther color: Close to N187B. Pollen color: Close to N187B. Pistils: Quantity per flower: One. Style length: About 3 cm. Style color: Close to NN155D. Stigma shape: Clavate. Stigma color: Close to NN155D. Ovary color: Close to 145B.

*Fruits.*—Length: About 1 cm to 1.5 cm. Diameter: About 6 mm to 7 mm. Color: Close to 144A.

Disease & pest resistance: Plants of the new *Agapanthus* have not been noted to be resistant to pathogens and pests common to *Agapanthus* plants.

Garden performance: Plants of the new *Agapanthus* have been observed to have good garden performance and to tolerate drought and temperatures ranging from −3° C. to about 38° C.

It is claimed:

1. A new and distinct *Agapanthus* plant named 'PMB011' as illustrated and described.

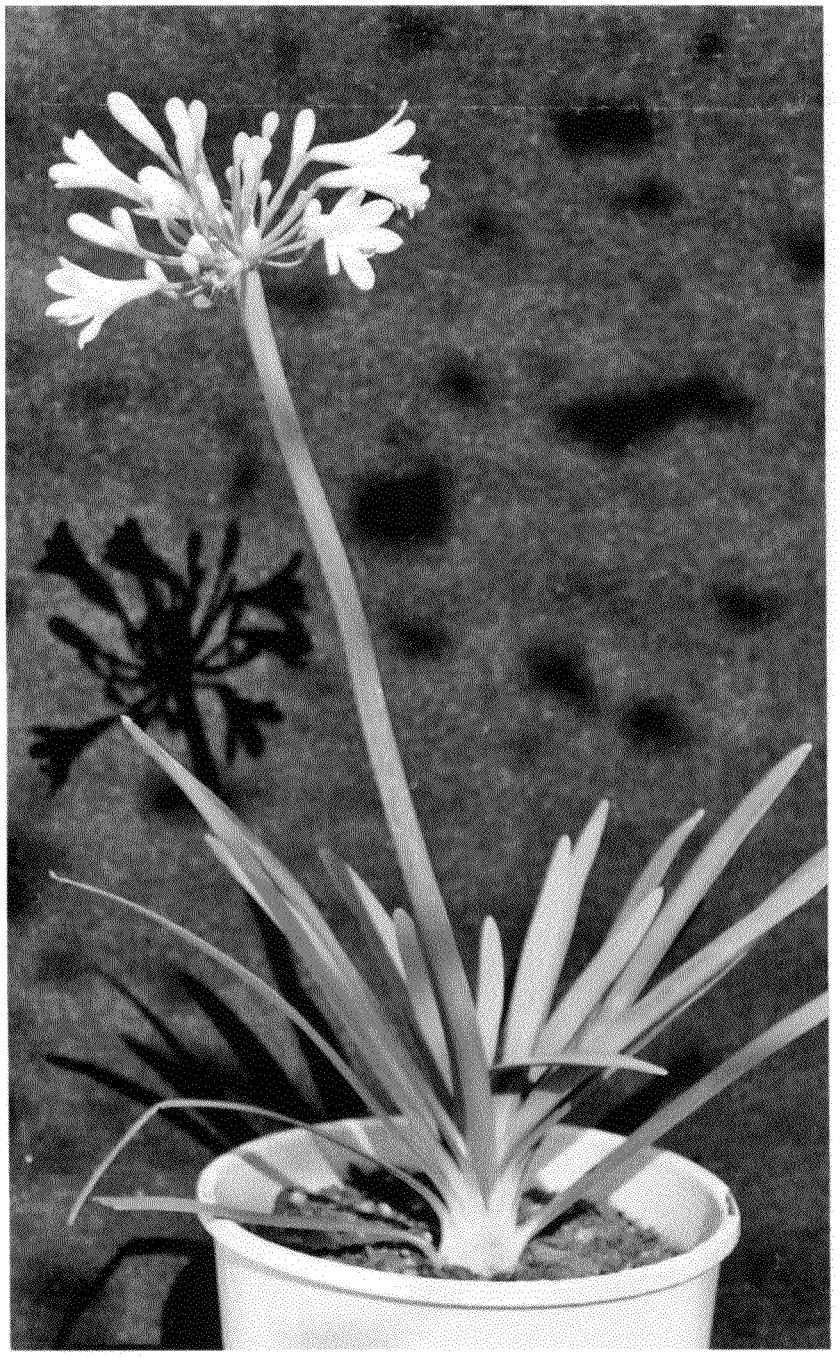

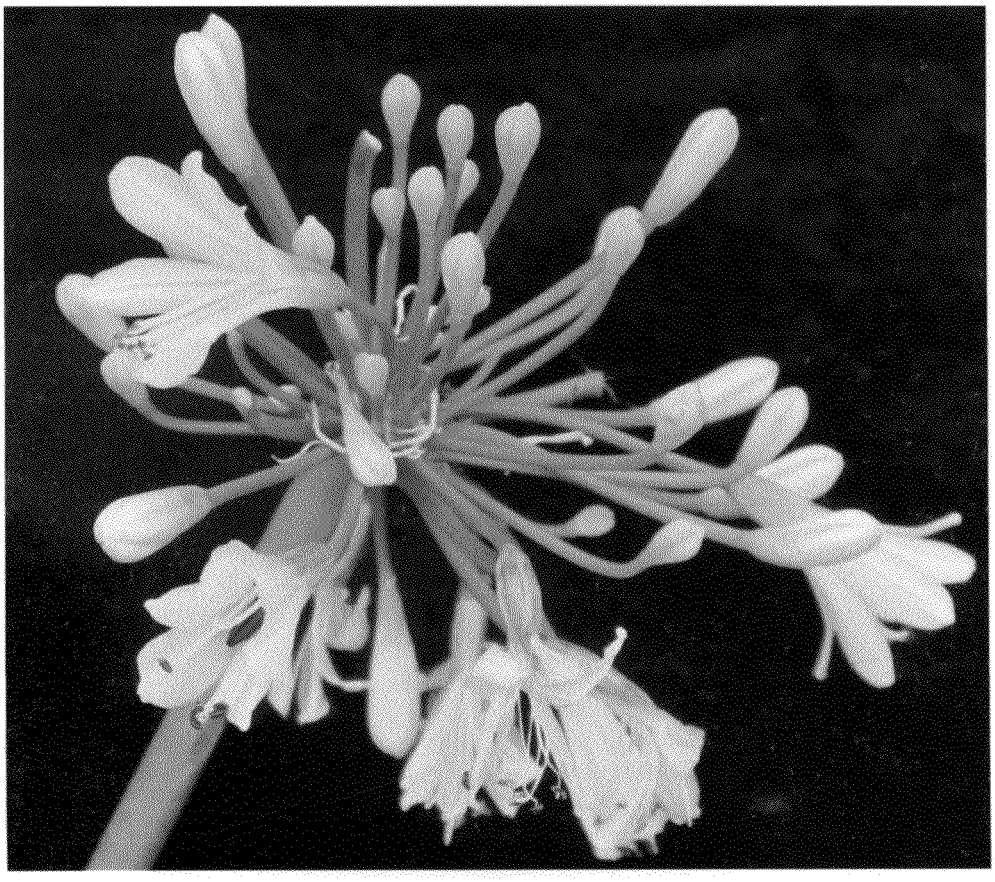

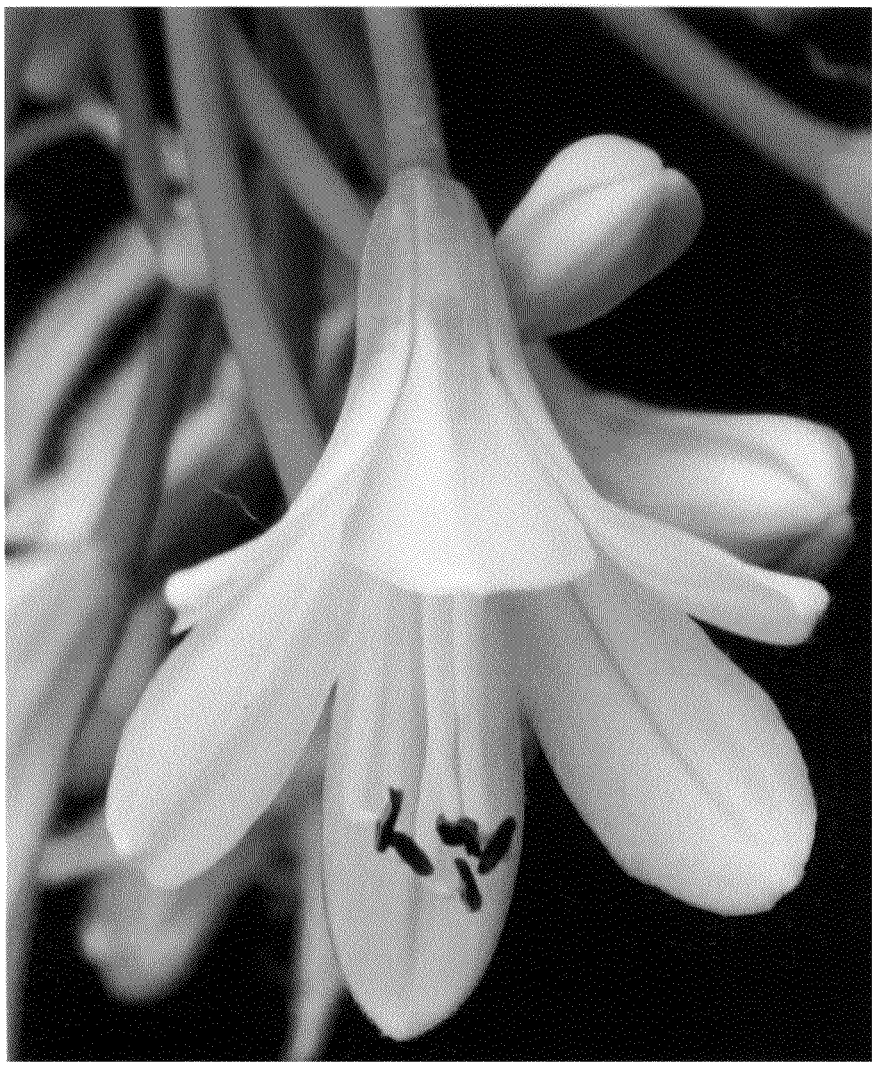

* * * * *